United States Patent [19]

Raines

[11] 4,211,588
[45] Jul. 8, 1980

[54] METHOD OF MANUFACTURING A VENTED PIERCING DEVICE FOR INTRAVENOUS ADMINISTRATION SETS

[75] Inventor: Kenneth C. Raines, Bethlehem, Pa.

[73] Assignee: National Patent Development Corporation, New York, N.Y.

[21] Appl. No.: 904,542

[22] Filed: May 10, 1978

[51] Int. Cl.² .................... A61M 5/00; B32B 31/16
[52] U.S. Cl. .................. 156/73.1; 128/214 R; 156/245; 156/308.6; 264/23; 285/137 R
[58] Field of Search ............... 156/73.1, 246, 69, 245, 156/73.5, 307; 128/214 C, 214 R; 285/137 R, 330, 331, 423; 264/23

[56] References Cited

U.S. PATENT DOCUMENTS

| | | | |
|---|---|---|---|
| 3,316,908 | 5/1967 | Burke | 128/214 C |
| 3,689,339 | 9/1972 | Klingler | 156/73.1 |
| 3,795,558 | 3/1974 | Dabney et al. | 156/73.1 |
| 3,944,261 | 3/1976 | Reed et al. | 156/73.1 |
| 4,009,714 | 3/1977 | Hammer | 128/214 C |

Primary Examiner—Michael G. Wityshyn
Attorney, Agent, or Firm—Shoemaker and Mattare, Ltd.

[57] ABSTRACT

A method of manufacturing a vented piercing device having a piercing spike which is considerably smaller in diameter than a standard device. The smaller diameter permits use of the device with small volume parenteral containers normally punctured with bottle needles. The method of assembly includes formation of a piercing device in two separate portions which are then welded together.

11 Claims, 6 Drawing Figures

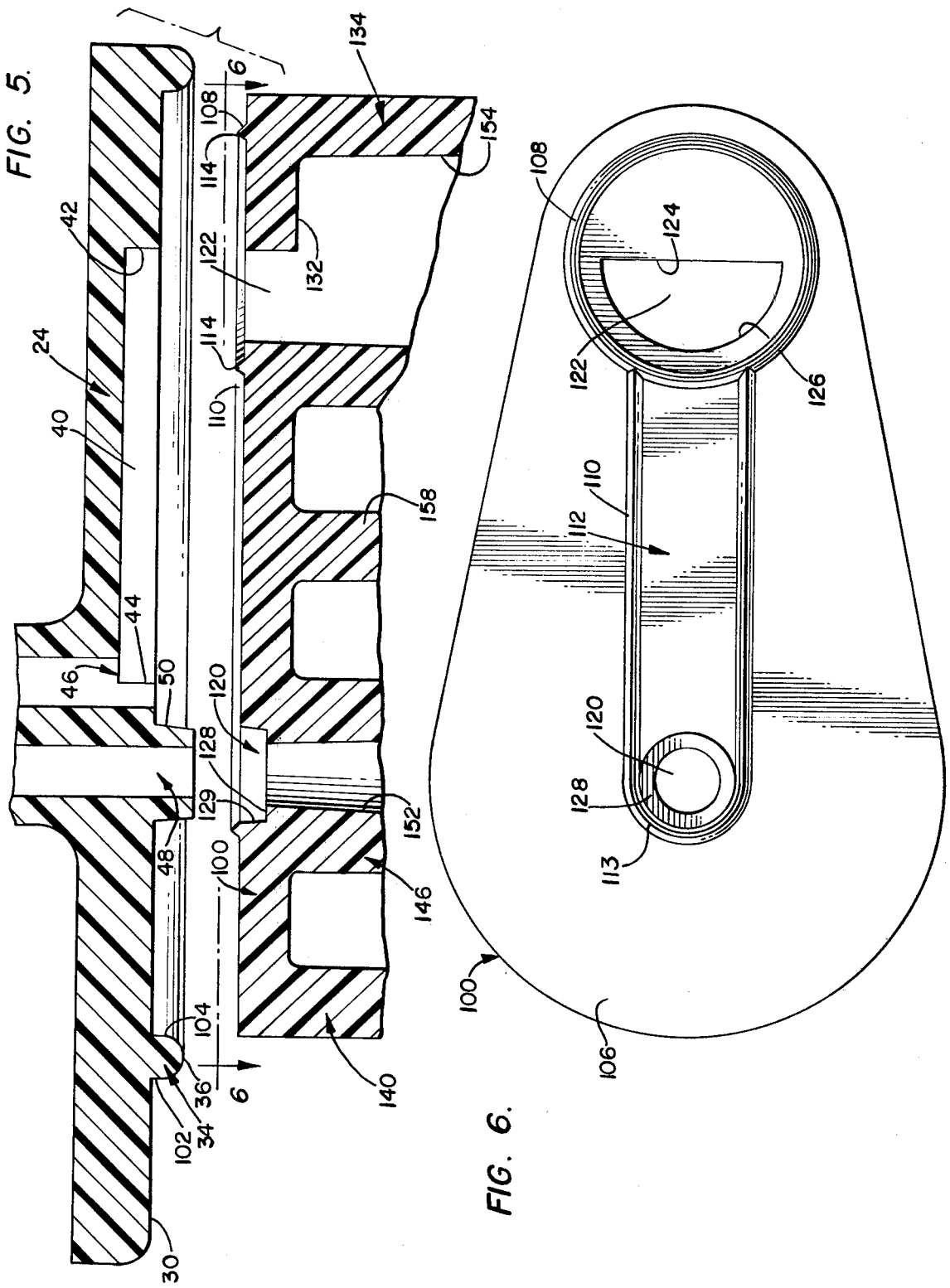

METHOD OF MANUFACTURING A VENTED PIERCING DEVICE FOR INTRAVENOUS ADMINISTRATION SETS

BACKGROUND OF THE INVENTION

The present invention relates in general to vented piercing devices used in intravenous administration sets, and more particularly, to a vented piercing device used with small volume parenteral fluid containers.

Heretofore, small volume parenteral fluid containers have been pierced with bottle puncture needles in assembling an intravenous setup. Using bottle needles presents several problems, however. Firstly, such needles have become expensive, and may become even more expensive as time goes on. It is noted that two needles are required to withdraw fluid from a container, one needle to define a fluid path and one needle to vent the bottle. Thus, the cost of such bottle piercing devices is raised even more. Secondly, puncturing such fluid containers with bottle needles requires dual punctures of such container. Every time a vial is punctured, there is a risk of contamination. It is evident that the fewer times a container needs to be punctured, the more aseptic the setup.

Accordingly, there is need for a device which can be used to withdraw parenteral fluid from small volume containers while requiring only a single puncture of the container. Such a device will reduce costs of intravenous sets as well as reduce risks of contamination.

In vented piercing devices, the air passage and the fluid passage must be separate and independent of each other. Accordingly, the manufacture of very small piercing devices of this nature places strict requirements on the tools used in that manufacturing process. For example, if the small piercing device is molded, the core pins used in the process to form the passages must be long and slender. Such core pin construction makes them fragile and quite susceptible to breaking. In fact, to form the passages in such devices it is usual for the air passages to be angled to permit the core pin to be properly positioned.

Accordingly, not only is there need for a small piercing device, there is need for method of manufacturing that device in an economical manner.

SUMMARY OF THE INVENTION

The device embodying the teachings of the present invention is capable of piercing small volume parenteral containers and is manufactured in an efficient manner. The piercing spike of the presently disclosed device is approximately 40% smaller in diameter than known devices.

The device includes two parts, an upper portion which includes a piercing spike and a lower body portion which includes fluid and air tubes. The portions are formed separately by injection molding, then welded together. Welding can be carried out ultrasonically or by use of a solvent. The fluid passage includes a boss on the upper portion and a boss receiving counterbore on the lower portion. The boss is welded to the lower portion during the welding process to form a shear joint. An energy director system can be formed on the lower portion and includes triangular ribs which have an apex thereof spaced from a base of the lower portion to contact a base of the upper portion. The triangular ribs are welded to the upper portion base during an ultrasonic welding process.

By being formed in two separate parts, the core pins and other such fragile tooling need not be long slender structures. The two-piece construction of the device disclosed herein thus reduces the overall length of the fragile core pins. The piercing spike of the present invention is on the order of 0.2 inches or less in diameter and includes fluid and air passages which must be separate from each other and are on the order of 0.05 inches in diameter and 0.5 inches long. Thus, any core pins used to form such passages will have a length to diameter ratio on the order of 10. If the device were formed as a single unit, the core pins may have a length to diameter ratio on the order of 18. A core pin having a length to diameter ratio of 10 is far less susceptible to breaking than a core pin having a length to diameter ratio of 18, and thus, the device embodying the teachings of the present invention, being formed in two parts which are attached together, can be manufactured in a much more economical manner than such a device manufactured as one piece.

The small size of the device embodying the present invention permits use thereof with small volume containers. The device thus replaces the bottle puncture needles and requires only a single penetration of vial. Thus, a single device replaces the dual needles required by the prior art. The savings in cost can be significant. Furthermore, the device of the present invention requires only a single penetration of a vial, thus reducing the possibility of contamination.

Furthermore, the method of manufacture disclosed herein permits manufacturing the device without an intricate cam action mold which would otherwise be required to define a vented airway.

While vented piercing devices for intravenous administration sets are known, for example, U.S. Pat. No. 3,316,908, the inventor is not aware of any vented piercing device made in the manner herein disclosed and which is suitable for use with small volume containers.

OBJECTS OF THE INVENTION

It is, therefore, a main object of the present invention to provide a device for use with small volume parenteral containers.

It is another object of the present invention to provide a method of economically manufacturing a device for use with small volume parenteral containers.

It is a specific object of the present invention to provide a method of manufacturing a device for use with small volume parenteral containers which includes injection molding of the device but does not require long slender core pins.

These together with other objects and advantages which will become subsequently apparent reside in the details of construction and operation as more fully hereinafter described and claimed, reference being had to the accompanying drawings forming part hereof, wherein like reference numerals refer to like parts throughout.

BRIEF DESCRIPTION OF THE DRAWINGS

FIG. 5 is a view showing the two parts of the device embodying the present invention in an adjacent but unjoined configuration.

FIG. 6 is a view taken along line 6—6 of FIG. 5.

DETAILED DESCRIPTION OF THE INVENTION

Figure 1:
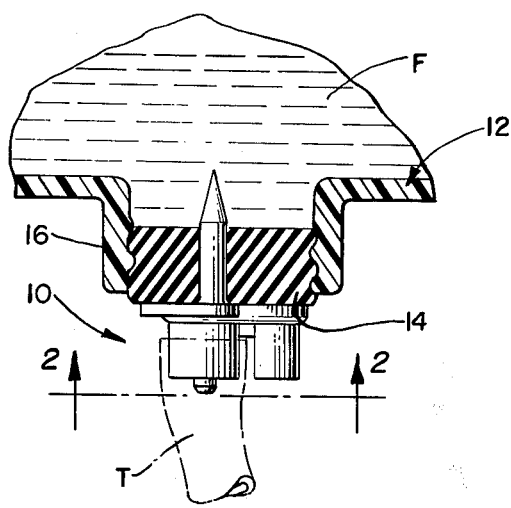
FIG. 1 is a view of the device of the present invention piercing a stopper of a small volume parenteral fluid container.

Shown in FIG. 1 is a vented piercing device 10 used to withdraw fluid, such as parenteral fluid F from a container, such as bottle 12 having a piercable stopper 14 lodged in neck portion 16 thereof. The bottle and stopper are similar to those usual to this art, and will not be further disclosed, and a tube T, or other device, is connected to the device 10 to receive fluid therefrom.

Figure 2:
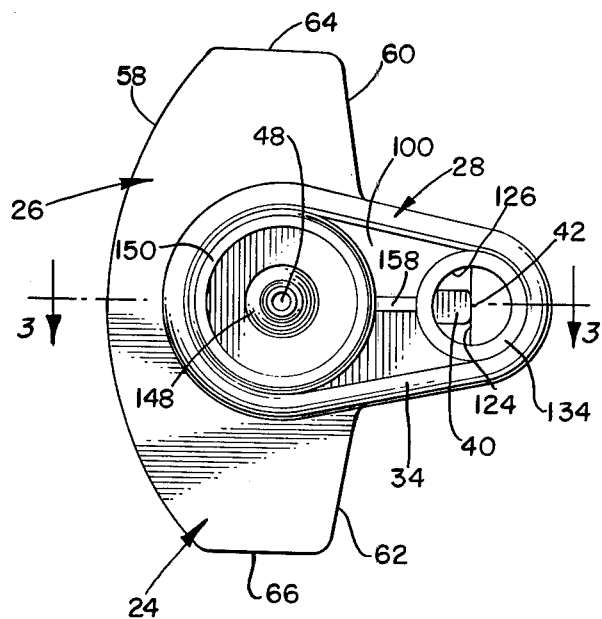
FIG. 2 is a view taken along line 2—2 of FIG. 1
Figures 3, 4:
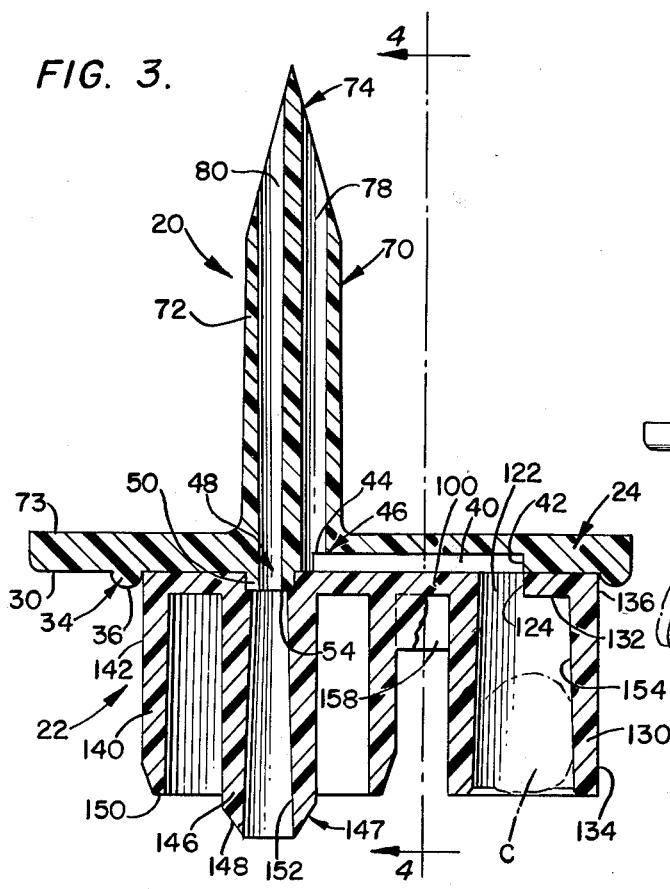
FIG. 3 is an elevation view taken along line 3—3 of FIG. 2.
FIG. 4 is an elevation view taken along line 4—4 of FIG. 3.

The piercing device 10 is best known in FIG. 3 to include an upper portion 20 and a body, or lower portion 22, which are connected together to form an integral unit as will be discussed below. The upper portion 20 forms a piercing device for penetrating stopper 14. The piercing device includes a base 24 which is shown in FIGS. 2 and 4 to be roughly T-shaped with a top portion 26 and an extending portion 28. The base has a planar surface 30 with a clamping rib 34 defined thereon to project outwardly from surface 30, and the rib section is roughly egg-shaped. The rib 34 is shown in FIG. 3 to be semicircular in shape with a top 36 thereof located above the surface 30 for a purpose to be later described. The base 24 further has an elongate trough 40 defined therein to have one end 42 adjacent the outer end of the extending portion 28 and to be located in the extending portion 28 and be coaxial therewith. A circular air port 44 is defined through the base at the inner end 46 of the trough and is defined so that the inner and 46 bisects that port. A fluid port 48 is defined in the base adjacent inner end 46 of the trough and includes a boss 50 surrounding same. The port 48 lies roughly on the center of the arcuate portion forming the large end of an egg-shaped rib section and has a lower rim 54 projection slightly beyond the rim 36 of the rib section. As shown in FIG. 2, the base 24 has an arcuate longitudinal perimeter 58 located on the side thereof which is remote from the extending portion and inwardly converging straight sides 60 and 62 on the other longitudinal sides thereof. The transverse ends 64 and 66 are both straight and are essentially parallel.

The upper portion further includes a piercing spike 70 having a trunk section 72 mounted at one end thereof on base surface 73 and extending outwardly therefrom in an essentially perpendicular manner, and a piercing point 74 on the other end thereof. As best shown in FIGS. 3 and 4, the piercing spike includes two elongate passages defined longitudinally thereof. The passages include air passage 78 having one end thereof in fluid communication with the base air port 44, and the other end thereof intersecting and being defined by the conical surface of the piercing point 74 to thus fluidly connect that piercing point with the air port 44 and thus form a riser section for the air path into the bottle 12. The other passage includes a fluid passage 80 having one end thereof in fluid communication with the fluid port 48 defined in the base 24, and the other end thereof intersecting and defined by the conical surface of the piercing point 74 to thus fluidly connect that piercing point with the fluid port 48 and thus form a downcomer section for the fluid path from the bottle 12. The passage 78 and 80 can each be slightly divergent from bottom to top, for example the passages can each have a 1½° included angle It is here noted that the piercing spike 70 is approximately 40% smaller in diameter than other previously known devices. The smaller diameter of the spike 70 permits use of the device 10 with small volume parenteral containers which have heretofore been punctured with bottle needles. The small nature of the device 10 is indicated in FIG. 1.

Lower portion 22 includes a base 100 shaped and sized to correspond to the shape and size of the rib 34. As shown in FIGS. 3 and 5, the perimeter of the base 100 is slightly smaller than the outer perimeter 102 of the rib 34, but slightly larger than the inner perimeter 104 thereof so that a jam fit is effected between the base 100 and rib 34 with the rib encircling the base to hold same in the FIG. 3 position.

As best shown in FIG. 6, the base has an upper surface 106 which has a first circular rib 108 extending upwardly therefrom at the small end of the egg-shaped base. An elongate trough forming rib 110 extends longitudinally of the base 100 to define a laterally extending trough 112 in the base 100, and intersects the rib 108 at one end thereof and has a circular end 113 at the other end thereof which is located adjacent the large end of the egg-shaped base. The ribs 108 and 110 are both triangular and have an apex section 114 thereof located above surface 106.

It is noted that ribs 108 and 110 define an energy director system, the function of which will be discussed below. The ribs are of constant height with respect to the surface 106, and thus the energy director system is of constant height throughout that system.

A fluid port 120 is defined in base 100 within and surrounded by the trough circular end 113 and a D-shaped air port 122 is defined in base 100 within and surrounded by the first circular rib 108 and the arcuate edge 126 of the air port 122 lies adjacent, but slightly spaced from, the circular rib 108 to define a marginal portion between the rib and the air port. A marginal portion 128 is defined between the fluid port 120 and the circular rib 108, and the marginal portion 128 is indented from the base upper surface 106 to define a boss receiving counterbore 129 which receives boss 50 defined on the unit upper portion as shown in FIG. 3.

A tubular air inlet 130 is integrally connected to the base 100 and depends downwardly from lower surface 132 of the base 100. The tube 30 is defined by a skirt which has an outer surface 134 flush with outer marginal surface 136 of the base 100.

A tubing connector 140 is tubular in shape and is located on the large end of the base 100, and has an outer surface 142 which is flush with base marginal outer surface 106. A second tube 146 is concentric with fluid port 120 and depends downwardly within the tube 140 to be coaxial therewith and has a lower terminal end 147 which has a chamfered rim 148 extending below rim 150 of the tube 140. The tube 146 has an inner bore 152 which is in fluid communication with fluid port 120 to receive fluid therefrom and conduct same into tube T. The bore 152 is tapered to have the lower end thereof larger than the upper end thereof. The air tube 130 has a bore 154 which is in fluid communication with the air port 122 to conduct air thereinto. A suitable filtering medium, such as cotton C, or the like, is generally placed within bore 154 to prevent contaminants from entering the fluid F via the air passages. A web 158 connects the tubes 130 and 140 and is integrally mounted on the lower surface of the base 100.

As best shown in FIGS. 2 and 3, when upper portion 20 and lower portion 22 are assembled, the trough end 42 is positioned adjacent the straight side 124 of the D-shaped air opening 122. The boss 50 is received in the counterbore 129 defined by the indented marginal portion 128 so that the downcomer 80 and the fluid bore 152 are colinear with the lower end of the downcomer being slightly smaller in diameter than the upper end of the bore 152. The trough defined in the lower surface 30 of the base 24 is thus received in and is shorter than the trough 112 defined by the upstanding ribs 110 on the upper surface 106 of the base 100. As shown in FIG. 4, the apex 114 of the trough defining ribs 110 contacts the lower surface 30 of the base 24 adjacent the elongate trough 40 on the outside of the trough 40, but immediately adjacent sides 160 and 162 thereof so that the apex 114 contacts surface 30 of the base into which the trough 40 is defined.

Thus, in the FIGS. 3 and 4 assembled configuration, an air path is defined by the bore 154, the air port 122, a laterally extending passage defined by the troughs 40 and 112, air port 44 and the riser section 78 of the piercing point. A fluid path is defined by the bore 152, fluid port 48 in the base 100 and the downcomer 80 of the piercing point. Filtered air is thus conducted into the fluid via the air passage and fluid is conducted from the container 12 into the tubing T via the fluid path.

In a preferred embodiment, the upper portion 20 includes a spike with an outer diameter of 0.156 inches and an overall length from top surface 73 of 0.789 inches. The passages 78 and 80 have, in the preferred embodiment, an inner diameter of 0.046 inches and the end thereof formed in piercing point 74. The piercing point is formed to have a maximum radius of 0.005 inches. These dimensions will illustrate the small size of the device 10. The small size of the device 10 makes the device unique, as such device can be used to replace the needle puncture devices heretofore used with small containers.

Having described the structure, the method of making and assembling same will now be presented. The top portion 20 is injection molded, and the bottom portion 22 is injection molded separately from the top portion. The bottom portion is held in a fixture, and the two portions are brought together. An ultrasonic horn is brought down over the device and engages, or touches, the flange, or base 24. Upon actuation of the ultrasonic horn, ultrasonic energy is imparted to the device to sonically seal the portions together.

Upon application of the ultrasonic energy to the device, the energy director system melts and thus the ribs 108 and 110 are sealed to the base 24 to thus sonically seal portions 20 and 22 together.

The ultrasonic energy further causes the boss 50 to melt along the exterior surface thereof and to become welded to the inner surface of the boss receiving counterbore 129. The welding of the exterior surface of the boss to the inner surface of the base 100 defining the counterbore 129 forms a shear joint.

The unit thus formed is integral and permits formation of a fluid path which is independent and separate from an air path. Such two-part molding followed by the ultrasonic welding permits formation of an extremely small piercing device which still has separate and independent fluid and air passages.

An alternative embodiment of the above-described method of manufacture includes solvent welding in place of the ultrasonic welding.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A method of manufacturing a vented piercing device for use with small volume parenteral containers, the method including the steps of:
   injection moldng a first portion of the piercing device;
   forming a fluid passage and an air passage in said first portion;
   injection molding a second portion of the piercing device including a step of forming a pair of separate passages one of which is part ofa fluid path for discharging parenteral fluid from a small volume container and the other of which is part of an air path for venting such small volume container, said first portion passages being positioned to fluidly connect with said second portion passages when said portions are connected together; and
   welding said first portion to said second portion to form an integral vented piercing device for use with small volume containers.

2. The method of claim 1, further including a step of forming an energy director system on said first portion, said energy director system including a triangular rib on said first portion with the apex of said triangular rib being adapted to contact said second portion.

3. The method of claim 2, wherein said welding step includes ultrasonically welding said portions together.

4. The method of claim 2, wherein said welding step includes solvent welding said portions together.

5. The method of claim 1, wherein said second portion includes a piercing spike having a length of less than 1 inch and an outer diameter of less than 0.2 inches.

6. The method of claim 5, wherein said passages have a length of about 0.5 inches and a diameter of less than about 0.05 inches.

7. The method of claim 1 wherein said passages are formed using core pins.

8. The method of claim 1, further including forming a boss on said second portion and a counterbore on said first portion in positions so that said boss is received in said counterbore when said portions are welded together to form a shear joint.

9. The method of claim 1, further including forming a clamping rib on said second portion which is sized to receive said first portion in a jam fitting relationship.

10. The method of claim 1, wherein said first portion has a top section which is egg-shaped in transverse cross-section.

11. The method of claim 1 wherein said fluid and air paths each includes a projection on said first portion extending away from said second portion when said portions are connected together, and said welding fluidly interconnects said second portion fluid and air paths with said projections.

* * * * *